(12) United States Patent
Iizuka

(10) Patent No.: US 8,898,837 B2
(45) Date of Patent: Dec. 2, 2014

(54) MEDICAL IMAGE DIAGNOSTIC APPARATUS

(75) Inventor: Satoshi Iizuka, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 14/239,381

(22) PCT Filed: Sep. 12, 2012

(86) PCT No.: PCT/JP2012/073279
§ 371 (c)(1),
(2), (4) Date: Feb. 18, 2014

(87) PCT Pub. No.: WO2013/042589
PCT Pub. Date: Mar. 28, 2013

(65) Prior Publication Data
US 2014/0208510 A1 Jul. 31, 2014

(30) Foreign Application Priority Data
Sep. 22, 2011 (JP) ................... 2011-207851

(51) Int. Cl.
*A47B 13/00* (2006.01)
*A61B 6/04* (2006.01)
*A61B 5/055* (2006.01)
*A61B 6/03* (2006.01)
*A61B 6/10* (2006.01)

(52) U.S. Cl.
CPC .............. *A61B 6/0407* (2013.01); *A61B 5/055* (2013.01); *A61B 5/0555* (2013.01); *A61B 6/04* (2013.01); *A61B 6/032* (2013.01); *A61B 6/102* (2013.01)
USPC ................. 5/601; 5/600; 5/81.1 HS

(58) Field of Classification Search
USPC ........ 5/600, 601, 81.1 R, 81.1 HS, 84.1, 943; 324/318; 378/208, 209
See application file for complete search history.

(56) References Cited

U.S. PATENT DOCUMENTS

| 4,641,823 | A  | * | 2/1987 | Bergman | ................... 5/81.1 HS |
| 7,874,030 | B2 | * | 1/2011 | Cho et al. | ........................... 5/601 |
| 8,166,586 | B2 | * | 5/2012 | Bridge et al. | ..................... 5/601 |
| 2008/0106262 | A1 | * | 5/2008 | Ohsawa | ....................... 324/318 |

FOREIGN PATENT DOCUMENTS

| JP | 6-165776 | 6/1994 |
| JP | 10-33527 | 2/1998 |

OTHER PUBLICATIONS

International Search Report in PCT/JP2012/073279.

* cited by examiner

*Primary Examiner* — Robert G Santos
*Assistant Examiner* — Richard G Davis
(74) *Attorney, Agent, or Firm* — Cooper & Dunham LLP

(57) ABSTRACT

In order to provide a medical image diagnostic apparatus in which a mechanism for drawing a top plate into a gantry can be connected to the top plate without the collision, a pin 17 is provided in an end portion of a top plate 70, and a hook 12 that is connected to the pin 17 is provided in the connecting mechanism 82 that is moved on a top plate receiving portion. According to a position of the connecting mechanism 82 on the top plate receiving portion, the position of the hook 12 varies to connect to the pin 17.

10 Claims, 16 Drawing Sheets (a)  (b)  (c)  (d)

MEDICAL IMAGE DIAGNOSTIC APPARATUS

TECHNICAL FIELD

The present invention relates to a medical image diagnostic apparatus, and relates to an apparatus including a mechanism for drawing a top plate, on which an object is placed, into the gantry.

BACKGROUND ART

As an example of a medical image diagnostic apparatus, there is a magnetic resonance imaging (MRI) apparatus. A conventional MRI apparatus includes a bed device. By placing an object on the top plate of the bed device and moving the top plate in the long axis (longitudinal) direction, the object is carried into the imaging space of the gantry. In addition, positioning of an imaging part is performed by adjusting the position of the top plate in the long axis direction. Depending on the imaging method, a method of moving the top plate in the long axis direction even during imaging in order to image the whole body of the object is also known.

In many conventional apparatuses, a driving mechanism for moving the top plate into the imaging space is provided in the bed device (for example, PTL 1). In this configuration, the transport distance of the top plate depends on the length of the bed in the long axis direction. Therefore, it has been difficult to transport the top plate over a distance larger than the length of the bed, for example, when imaging the whole body of the object.

PTL 2 proposes an MRI apparatus including a driving mechanism on the gantry side. PTL 2 proposes a configuration in which a carriage including a driving mechanism is disposed on the gantry side and a wheeled top plate is connected to the hook of the carriage so as to be drawn into the gantry. Since the driving mechanism is mounted on the gantry side, the transport distance of the top plate does not depend on the length of the bed.

CITATION LIST

Patent Literature
[PTL 1] Japanese Patent No. 3143131
[PTL 2] U.S. Pat. No. 4,641,823

SUMMARY OF INVENTION

Technical Problem

However, how the carriage and the top plate are brought close to each other for connection therebetween is not described in detail in PTL 2. An object is placed on the top plate, and is usually inserted into the gantry from the head side. For this reason, the carriage disposed in the gantry is connected to the top plate end on the side where the head of the object is placed. If the carriage and the top plate collide with each other when the hook of the carriage is connected to the top plate, impact due to the collision occurs in the immediate vicinity of the head of the object. In addition, when the carriage rides on the top plate, there is a possibility that the carriage may collide with the object. In addition, even when moving the top plate from the gantry onto the bed after imaging and releasing the connection, accurate positioning and a release method, which does not cause an impact, are desired.

It is an object of the present invention to provide a medical image diagnostic apparatus in which a mechanism for drawing a top plate into a gantry can be connected to the top plate without colliding with the top plate.

Solution to Problem

In order to achieve the above-described object, a medical image diagnostic apparatus of the present invention includes: a gantry having an imaging space; a bed device including a top plate on which an object is placed; and a top plate drawing mechanism that draws the top plate into the imaging space of the gantry. At least a part of the top plate drawing mechanism is disposed in the gantry. The top plate drawing mechanism includes a top plate receiving portion having an end disposed opposite the bed device, a connecting mechanism that is movable on the top plate receiving portion, and a driving unit that moves the connecting mechanism on the top plate receiving portion. A first member having a predetermined shape that is engaged with the connecting mechanism is provided in an end portion of the top plate, A second member having a shape that is engaged with the first member of the top plate and a movable portion that retracts the second member up to a predetermined position are provided in the connecting mechanism. The top plate drawing mechanism moves the connecting mechanism toward the bed device on the top plate receiving portion, retracts the second member up to the predetermined position when the connecting mechanism becomes close to a predetermined origin of a top surface on the one end side of the top plate receiving portion, stops the connecting mechanism when the connecting mechanism reaches the origin, and releases the retraction of the second member while making the connecting mechanism move away from the bed device, so that the second member is engaged with the first member of the top plate and the top plate is drawn into the gantry.

Advantageous Effects of Invention

According to the medical image diagnostic apparatus of the present invention, in a state where the second member of the connecting mechanism is retracted, the connecting mechanism can be brought close to the first member of the top plate and be stopped at the origin position. By releasing the retraction of the second member while making the connecting mechanism move away from the bed device, it is possible to draw the top plate into the gantry simultaneously with the connection between the connecting mechanism and the top plate. Therefore, it is possible to draw the top plate into the gantry without the connecting mechanism colliding with the top plate on which the object is placed.

DESCRIPTION OF EMBODIMENTS

Figure 1:
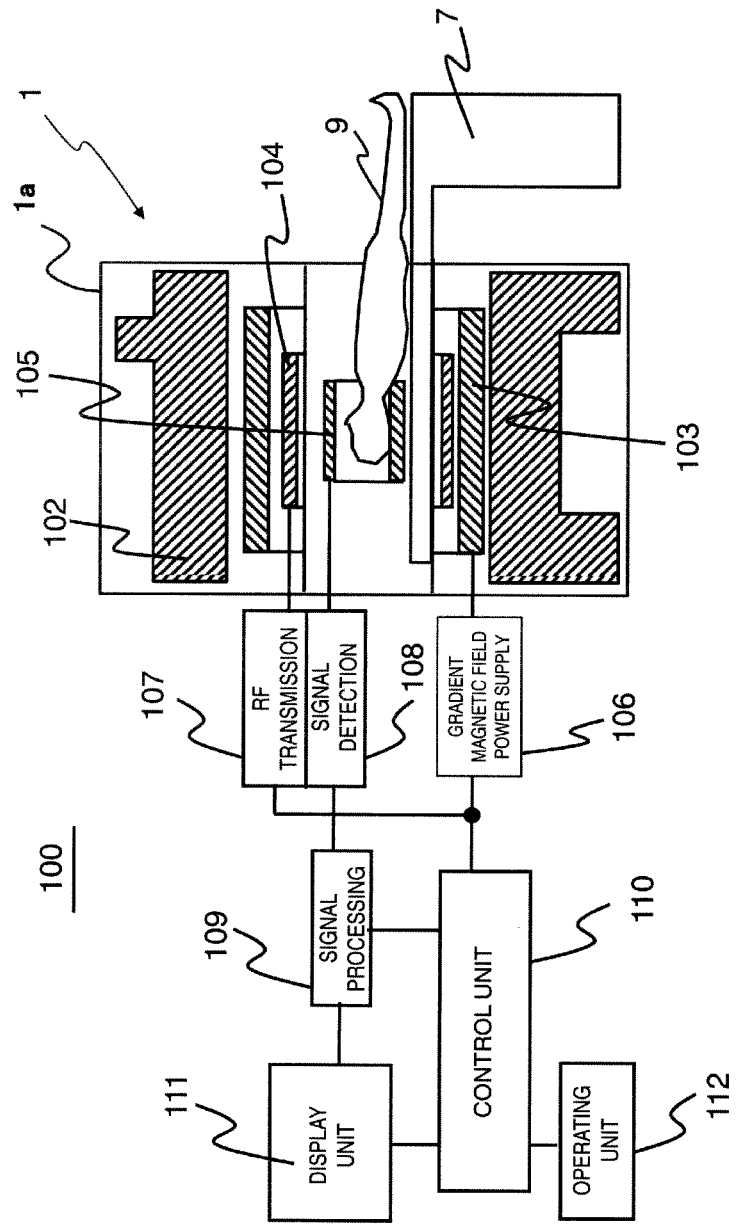
FIG. 1 is a block diagram of a medical image diagnostic apparatus of a first embodiment.

Hereinafter, an embodiment of the present invention will be described in detail with reference to the diagrams. In addition, in all diagrams for explaining each embodiment of the present invention, the same reference numerals are given to components having the same functions, and repeated explanation thereof will be omitted.

<First Embodiment>

As an example of a medical image diagnostic apparatus of a first embodiment, an MRI apparatus including a cylindrical gantry will be described. However, the shape of the gantry of the MRI is not limited to the cylindrical shape, and it is possible to apply a gantry in which a pair of plate-shaped magnets are disposed opposite each other.

Figure 2:
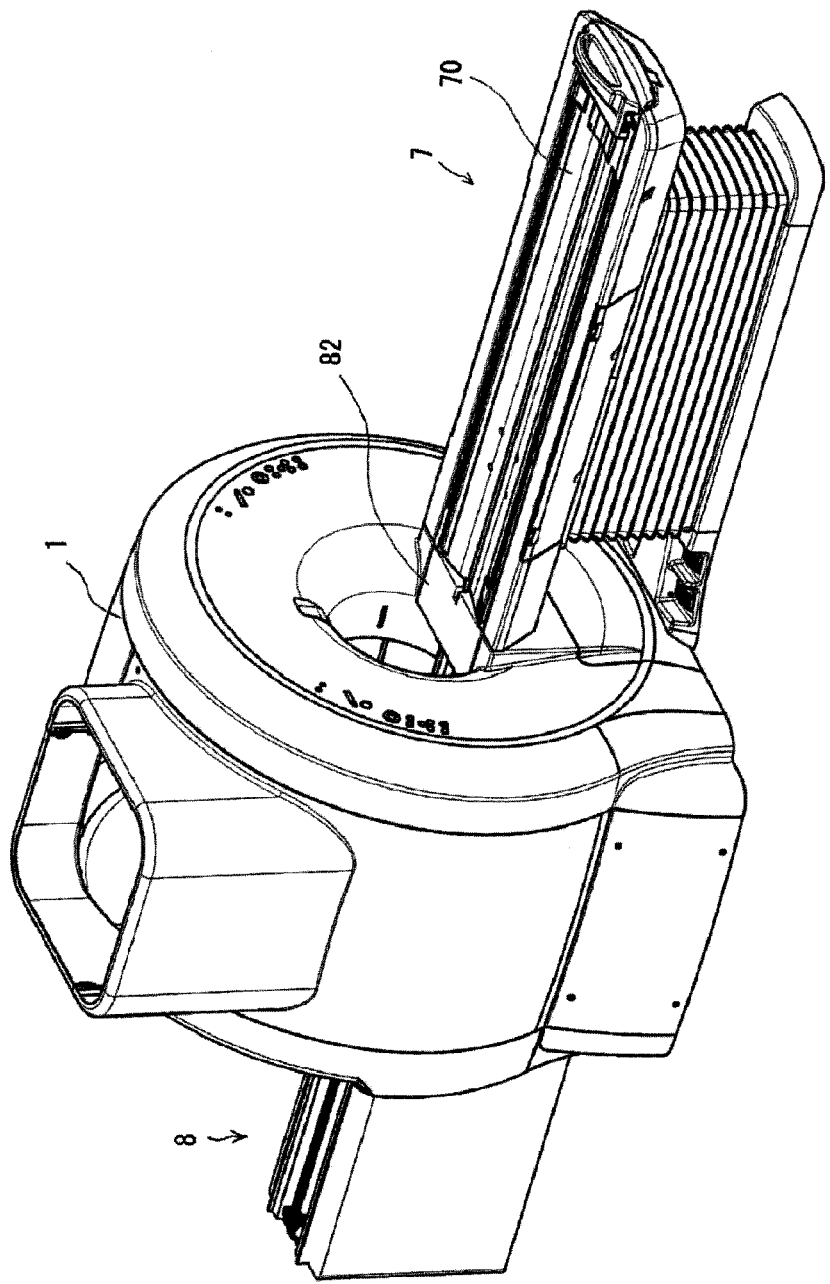
FIG. 2 is a perspective view of the medical image diagnostic apparatus of the first embodiment.

FIG. 1 is a functional block diagram of an example of an MRI apparatus including a gantry 1. FIG. 2 is a perspective view of the gantry 1 and a bed device 7. As shown in FIG. 1, an MRI apparatus 100 includes a cylindrical magnet 102 disposed with a horizontal direction as its axis direction, a gradient magnetic field coil 103, a high-frequency magnetic field (RF) coil 104, and an RF probe 105 that are disposed on the inner side of the cylindrical magnet 102, and the bed device 7. The magnet 102, the gradient magnetic field coil 103, and the RF coil 104 are covered by a gantry cover 1a having an approximately cylindrical appearance as shown in FIG. 2. The hollow space in the center of the approximately cylindrical gantry cover 1a is an imaging space.

The bed device 7 includes a top plate 70 on which an object 9 is placed and a bed driving mechanism 71 for moving the top plate 70 up and down. The gantry 1 includes a mechanism 8 for drawing the top plate 70 of the bed device 7 into the imaging space as will be described later. The bed device 7 and the top plate drawing mechanism will be described in detail later.

The MRI apparatus 100 further includes a gradient magnetic field power supply 106, an RF transmission unit 107, a signal detection unit 108, a signal processing unit 109, a control unit 110, a display unit 111, and an operating unit 112.

The magnet 102 generates a static magnetic field in the imaging space of the object 9. The gradient magnetic field coil 103 includes a coil to generate a gradient magnetic field in three directions of X, Y, and Z, and generates a gradient magnetic field in the imaging space according to the signal from the gradient magnetic field power supply 106. The RF coil 104 applies (emits) an RF to the imaging space according to the signal from the RF transmission unit 107. The RF probe 105 detects an NMR (nuclear magnetic resonance) signal generated by the object 9. The signal received by the RF probe 105 is detected by the signal detection unit 108, is subjected to signal processing by the signal processing unit 109, and is input to the control unit 110. The control unit 110 reconstructs an image from the input signal and displays the image on the display unit 111. In addition, the control unit 110 controls the operations of the gradient magnetic field power supply 106, the RF transmission unit 107, the signal detection unit 108, and the like according to the time chart of control stored in advance and the imaging parameters input by the operator through the operating unit 112. In addition, the time chart of control is referred to as a pulse sequence in general.

Figure 3:
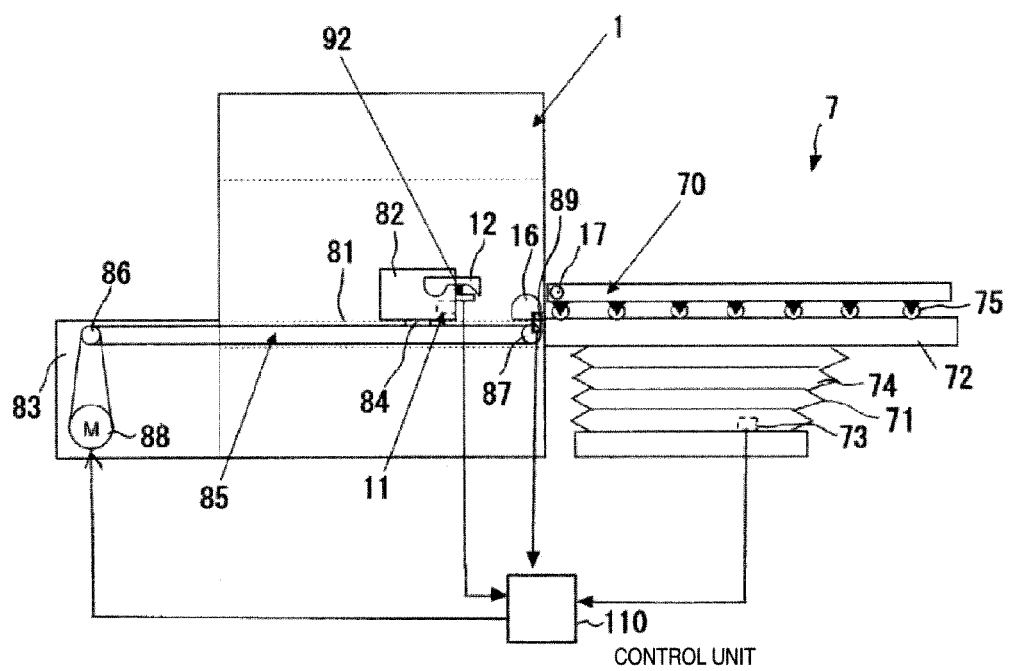
FIG. 3 is a block diagram of a top plate drawing mechanism of the medical image diagnostic apparatus of the first embodiment.
Figure 4:
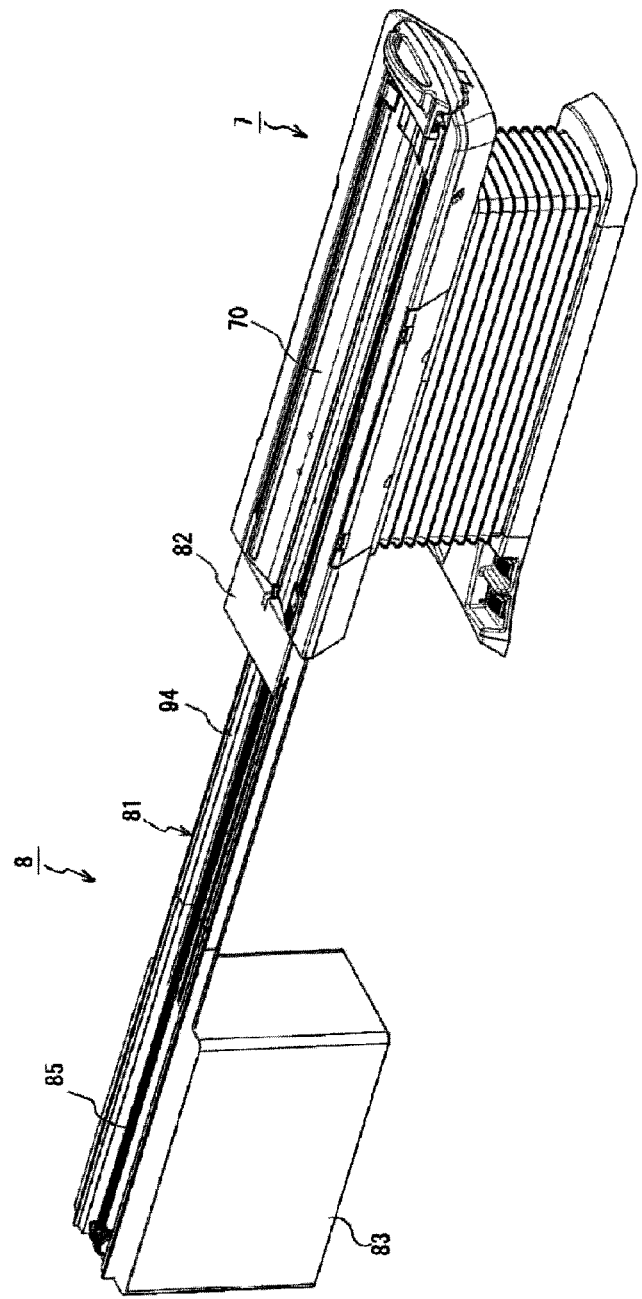
FIG. 4 is a perspective view of a bed device 7 and a top plate drawing mechanism 8 of the first embodiment.
Figure 5:
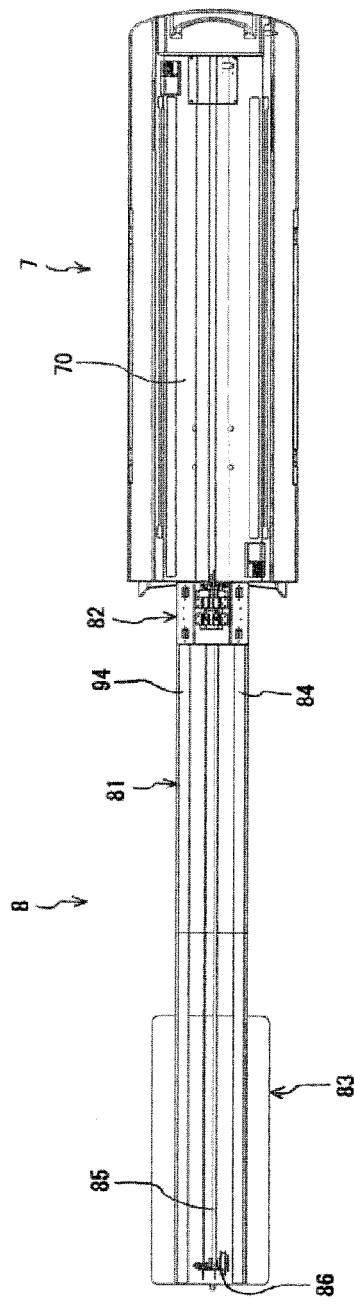
FIG. 5 is a top view of the bed device 7 and the top plate drawing mechanism 8 of the first embodiment.
Figure 6:
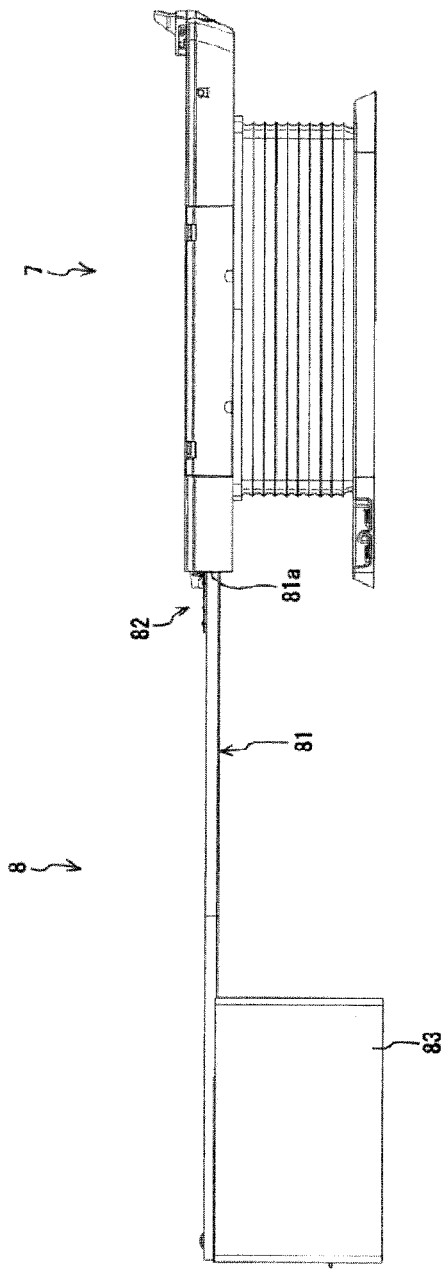
FIG. 6 is a side view of the bed device 7 and the top plate drawing mechanism 8 of the first embodiment.
Figure 7:
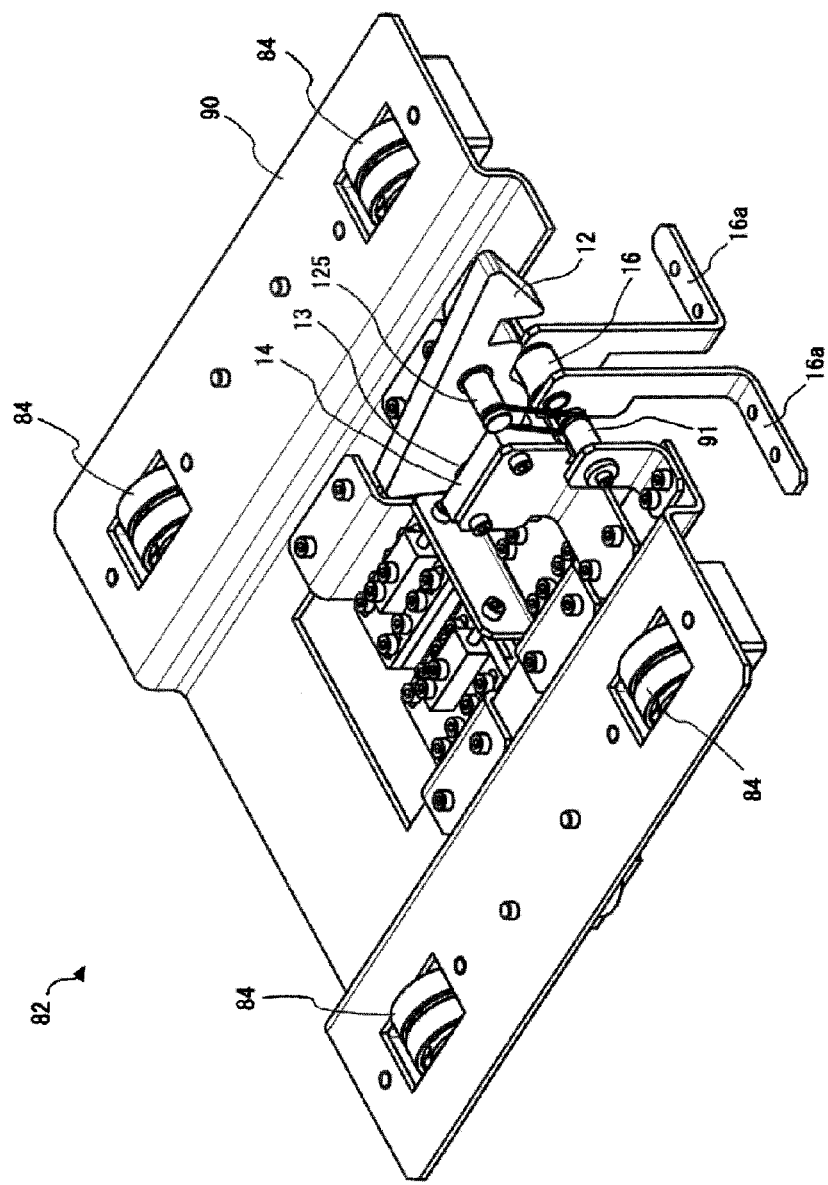
FIG. 7 is a perspective view in a state where the cover of a connecting mechanism in the first embodiment is removed.

Next, the bed device 7 and the mechanism 8 for drawing the top plate 70 into the imaging space will be described. FIG. 3 is a block diagram showing the schematic configuration of the gantry 1, the bed device 7, and the top plate drawing mechanism, and FIGS. 4, 5, and 6 are a perspective view, a top view, and a side view of the bed device 7 and the top plate drawing mechanism 8, respectively. FIG. 7 is a perspective view in a state where the cover of a connecting mechanism 82, which will be described, is removed. FIGS. 5 and 6 show a state where the cover of the connecting mechanism 82 is removed.

In addition to the top plate 70 and the top plate driving mechanism 71 described above, the bed device 7 includes a top plate support 72 that supports the top plate 70, a main body 74 that supports the top plate support 72 so as to be movable up and down, and a vertical position sensor 73 that detects the vertical position of the top plate 70. The top plate driving mechanism 71 and the vertical position sensor 73 are built in the main body 74. A plurality of wheels 75 are provided on the bottom surface of the top plate 70, so that the top plate 70 can travel on the top plate support 72 and a top plate receiving portion 81 of the top plate drawing mechanism 8 to be described later.

The top plate drawing mechanism 8 includes the top plate receiving portion 81, the connecting mechanism 82 including a wheel 84 on its bottom surface, and a top plate receiving portion support 83. The longitudinal direction of the top plate receiving portion 81 matches the longitudinal direction of the top plate 70, and the top plate receiving portion 81 has a length equal to or greater than the length of the top plate 70. One end of the top plate receiving portion 81 is inserted into the hollow space (imaging region) in the center of the gantry 1, and is supported by being fixed to a lower portion of the inner wall of the gantry 1. The other end is supported by being mounted on the top plate receiving portion support 83. As shown in FIG. 6, an end surface 81a of one end of the top plate receiving portion 81 inserted into the gantry 1 is disposed so as to face an end surface of the top plate support 72 in a state where the bed device 7 has risen to the top with a predetermined very small gap interposed therebetween.

As shown in FIG. 5, on both sides of the top surface, the top plate receiving portion 81 has a flat traveling surface 94 for making the wheel 84 of the connecting mechanism 82 and the wheel 75 of the top plate 70 travel. The region between a pair of traveling surfaces 94 is recessed in a groove shape, and a timing belt 85 is disposed along the longitudinal direction. In addition, at both ends of the groove-shaped recess of the top plate receiving portion 81, pulleys 86 and 87 for rotating the timing belt 85 are disposed. The pulley 86 is rotated and driven by a motor 88 built in the top plate receiving portion support 83. As a result, the timing belt 85 is driven.

The connecting mechanism 82 is engaged with a predetermined position of the timing belt 85 by a member (not shown), and travels in the longitudinal direction of the top plate receiving portion 81 by driving of the timing belt 85.

Figure 8:
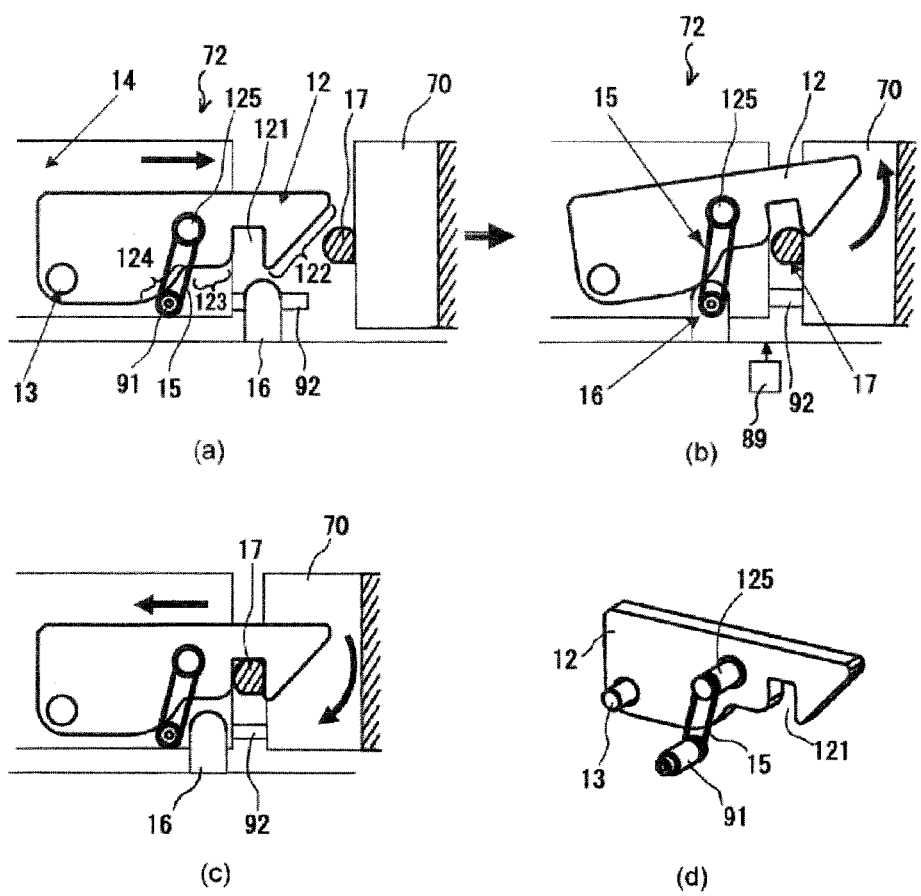
FIGS. 8(a) to 8(c) are explanatory views showing the operation of a hook 12 of the first embodiment.
FIG. 8(d) is a perspective view of the hook.

As shown in FIG. 7, the connecting mechanism 82 includes a base 90, in which the wheels 84 are mounted on both sides, and a hook 12 disposed in the middle of the end portion of the main body 74 in the bed device 7. The hook 12 is fixed to a plate portion 14 of the base 90 so as to be rotatable by a shaft 13 fixed to the base portion. FIGS. 8 (a) to 8(c) are side views showing the shape of the hook 12 and the state in the middle of the operation, and FIG. 8(d) is a perspective view of the hook 12. As shown in FIGS. 7 and 8(a) to 8(d), the hook 12 has a shape including a recess 121 for being engaged with the top plate 70, a first inclined surface 122 provided closer to the distal side than the recess 121 is, and a horizontal portion 123 and a second inclined surface 124 that are provided in order so as to be closer to the rotary shaft 13 side than the recess 121 is.

As shown in FIGS. 8(a) to 8(c), a connecting pin 17 is fixed to the end surface of the top plate 70 on the gantry 1 side with the width direction of the top plate 70 as its axis direction. The first inclined surface 122 of the tip of the hook 12 is formed so as not to collide with the hook 12 up to the vicinity of the recess 121 even if the connecting pin 17 approaches.

In addition, on the top surface of the end portion of the top plate receiving portion 81 on the bed device 7 side, a push-up portion 16 to push up the hook 12 of the connecting mechanism 82 is fixed to the predetermined position and height by a fixture 16a. The horizontal portion 123 of the hook 12 is provided at a position higher than the tip of the push-up portion 16, so that the horizontal portion 123 is not in contact with the push-up portion 16 even if the hook 12 approaches the push-up portion 16. When the second inclined surface 124 is in contact with the tip of the push-up portion 16, the hook 12 is pushed up while rotating around the shaft 13. In this case, the inclination angle of the second inclined surface 124 is determined such that the recess 121 is lifted higher than the connecting pin 17 without being in contact with the connecting pin 17.

In addition, in the hook 12, a projection 125 is provided between the shaft 13 and the recess 121. The projection 125 is connected to a projection 91, which is fixed to the base 90, by an elastic member 15, such as a rubber band. The elastic member 15 is biased in a direction in which the hook 12 is pushed down.

On the top surface of the top plate receiving portion 81, an origin sensor 89 for detecting that the connecting mechanism 82 has moved to the origin is disposed at a predetermined origin position near the push-up portion 16. An optical sensor or the like can be used as the origin sensor 89.

In addition, a connection detection sensor 92 that detects that the hook 12 has approached so as to be able to be engaged with the connecting pin 17 of the top plate 70 is provided on the cover of the connecting mechanism 82. The connection detection sensor 92 can be formed by a pin, which is pushed in contact with the end surface of the top plate 70, and an optical sensor that detects that the pin has been pushed. Alternatively, it is possible to use a contact type sensor, such as a microswitch.

The connection detection sensor 92, the origin sensor 89, and the motor 88 are connected to the control unit 110. In addition, the vertical position sensor 73 of the bed device 7 is also connected to the control unit 110.

In addition, since the gantry 1 of the present embodiment is an MRI apparatus, the connecting mechanism 82 and the top plate receiving portion 81 are formed of a non-magnetic material, such as aluminum or resin.

An operation when the top plate 70 is drawn into the gantry 1 will be described with reference to the flowchart of FIG. 9.

Figure 9:
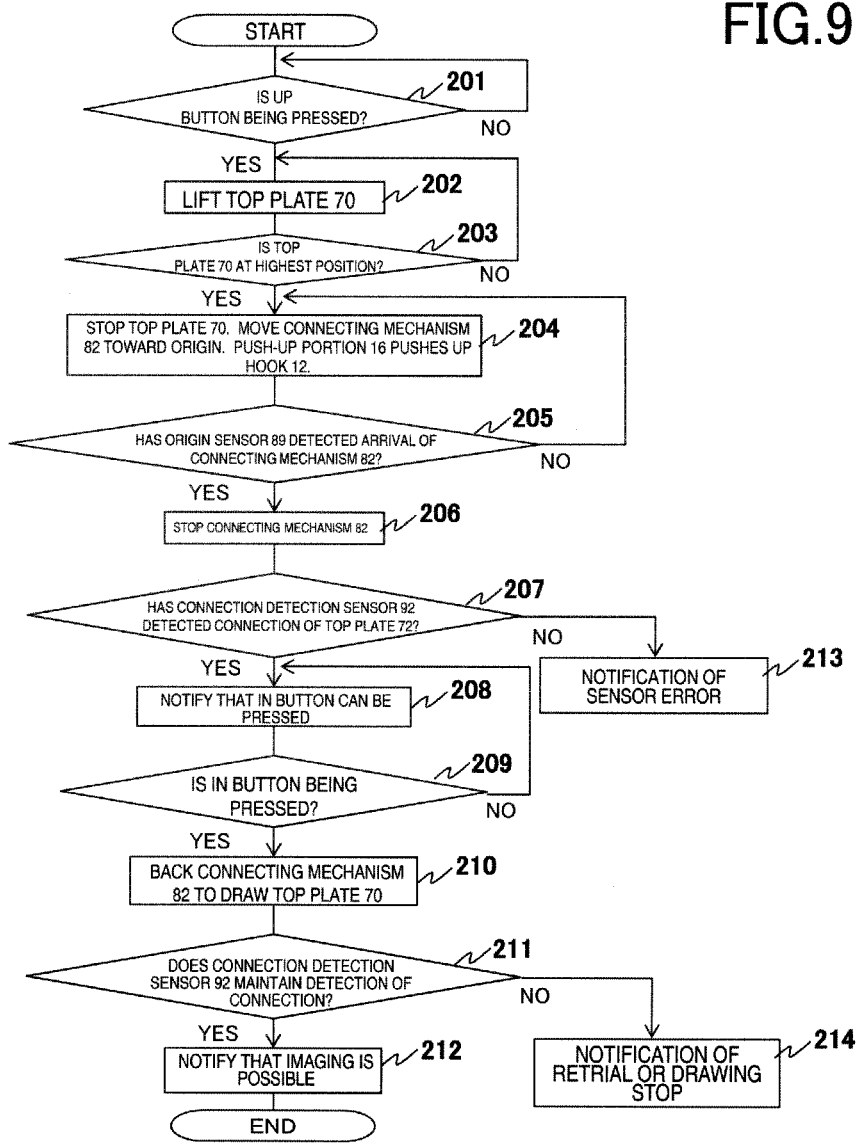
FIG. 9 is a flowchart showing the operation of drawing a top plate 70 using the top plate drawing mechanism 8 of the first embodiment.

The operation shown in FIG. 9 is realized when the control unit 110 controls each unit. The operating unit 112 includes an UP button for instructing the rise of the top plate 70, an IN button for instructing the drawing of the top plate 70 into the gantry 1, and an OUT button for instructing the removal of the top plate 70 from the gantry 1. These buttons may be disposed together with other operation buttons on the operation panel, or may be disposed on the side surface or the like of the gantry 1.

When the operator operates the UP button of the operating unit 112 to instruct the rise of the top plate 70, the driving mechanism 71 of the bed device 7 lifts the top plate 70 (steps 201 and 202). When the vertical position sensor 73 of the bed device 7 detects that the top plate 70 has reached the highest position as a result of a continuous rise until the top plate 70 reaches the highest position, the driving mechanism 71 is stopped since the top plate support 72 has reached the same height as the top plate receiving portion 81. Then, the motor 88 is driven to move the connecting mechanism 82 toward the origin (toward the bed device 7) (steps 203 and 204). Accordingly, the connecting mechanism 82 approaches the push-up portion 16 as shown in FIG. 8(a).

Since the tip of the hook 12 includes the first inclined surface 122, it is not in contact with the connecting pin 17. As shown in FIG. 8(b), when the push-up portion 16 reaches the second inclined surface 124 after passing the horizontal portion 123 of the hook 12, the push-up portion 16 pushes up the second inclined surface 124, so that the recess 121 of the hook 12 is lifted higher than the connecting pin 17 (step 204).

When the origin sensor 89 detects that the connecting mechanism 82 has reached the origin, the connecting mechanism 82 is stopped by stopping the motor 88 (steps 205 and 206).

In this case, when it is detected that the pin of the connection detection sensor 92 has been pushed by the end surface of the top plate 70 so as to be in contact with the top plate 70, the operator is notified that the top plate 70 is drawn into the gantry 1 if the drawing button (IN button) of the operating unit 112 is operated (steps 207 and 208). As a notification method, for example, a method of flashing the lights built into the IN button is used. In addition, when the connection detection sensor 92 does not detect contact with the top plate 70 in step 207 even though the origin sensor 89 detects that the connecting mechanism 82 has reached the origin in step 205, the operator is notified of the sensor error by the display or the like since there is a problem in the connection detection sensor 92 (step 213).

Figure 10:
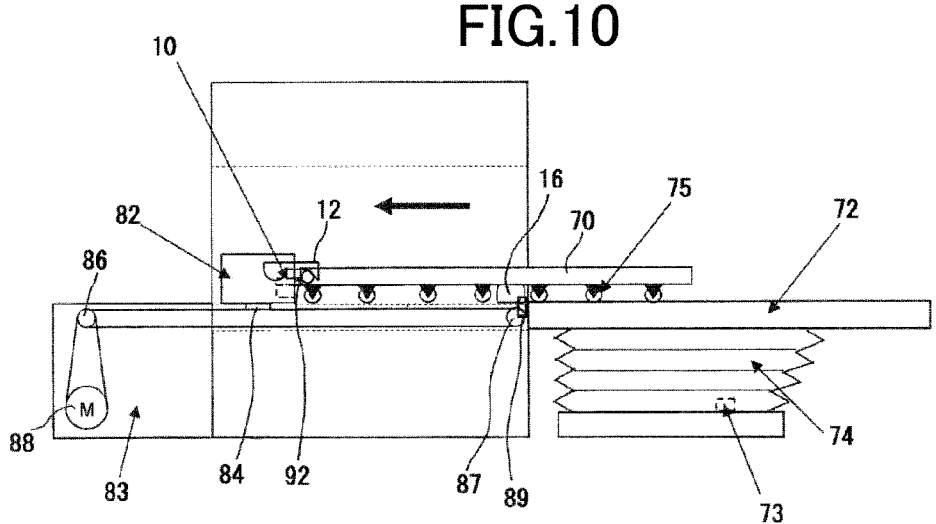
FIG. 10 is a block diagram showing a mechanism for drawing the top plate into a gantry 1 of the medical image diagnostic apparatus of the first embodiment.

When the operator operates the IN button (step 209), the motor 88 is reversely rotated to back the connecting mechanism 82 so that the connecting mechanism 82 is moved toward the top plate receiving portion support 83 (step 210). Then, as shown in FIG. 8(c), the push-up portion 16 deviates from the hook 12. As a result, the hook 12 is lowered to be engaged with the connecting pin 17. In this state, the top plate 70 travels on the top plate receiving portion 81 together with the connecting mechanism 82 and is drawn into the imaging space of the gantry 1 as shown in FIG. 10 (step 210).

When the connection detection sensor 92 continues to detect contact with the top plate 70, engagement between the top plate 70 and the hook 12 is maintained, and the top plate 70 is in a state drawn into the gantry 1. Accordingly, the operator is notified that preparation for imaging is completed and it is possible to perform imaging (steps 211 and 212). The operator can image a desired part of the object 9 by operating the operating unit 112 to execute an imaging sequence.

On the other hand, when the connection detection sensor 92 does not detect contact with the top plate 70 in step 211, the hook 12 is not engaged well with the connecting pin 17, and the top plate 70 does not move together with the connecting mechanism 82. Accordingly, the process returns to step 204 to notify the operator that retrial or stopping of the operation is to be performed (step 214).

Figure 11:
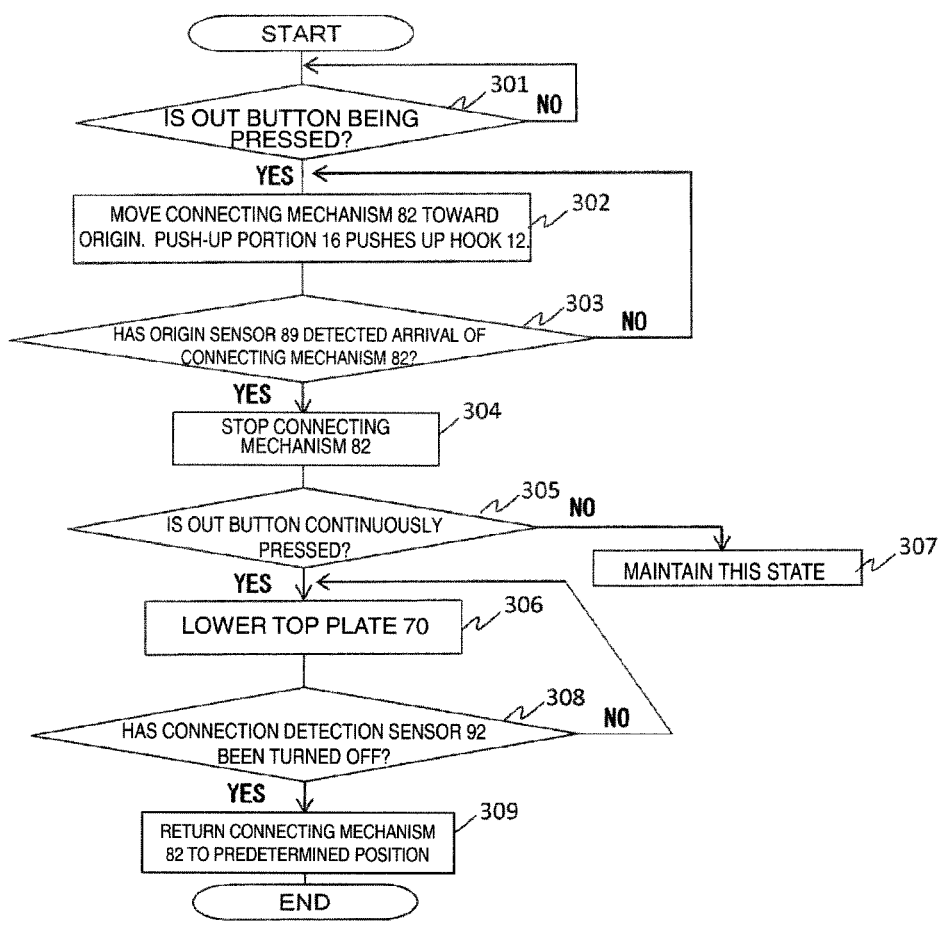
FIG. 11 is a flowchart showing the operation of taking out the top plate 70 from the gantry 1 using the top plate drawing mechanism 8 of the first embodiment.

Next, the operation of each unit when pulling out the top plate 70 up to the bed device 7 after the end of imaging or in the middle of imaging will be described with reference to the flowchart of FIG. 11.

When the operator operates the OUT button of the operating unit 112, the control unit 110 drives the motor 88 to move the connecting mechanism 82 toward the origin (steps 301 and 302). The hook 12 is pushed up by the push-up portion 16 by returning to the origin, and is displaced from the state of being engaged with the connecting pin 17 shown in FIG. 8 (c) to the lifted state shown in FIG. 8 (b). When the origin sensor 89 detects that the connecting mechanism 82 has reached the origin, the connecting mechanism 82 is stopped by stopping the motor 88 (steps 303 and 304).

When the OUT button is continuously pressed at this point in time, the operator gives an instruction to further lower the top plate 70. Accordingly, the top plate 70 is lowered by the driving mechanism 71 of the bed device 7 in a state where the connecting mechanism 82 is disposed at the origin (steps 305 and 306). Thus, it is possible to release the connection between the top plate 70 and the connecting mechanism 82 without having an impact on the top plate 70.

Since the connection is released when the connection detection sensor 92 is turned off, the motor 88 is driven to return the connecting mechanism 82 to a predetermined position (home position) (steps 308 and 309).

In addition, when the OUT button is not continuously pressed in step 305, the top plate 70 is not lowered and maintains the state (step 307).

In the present embodiment, since the hook 12 can be pushed up by the push-up portion 16 and be accurately positioned and stopped by the origin sensor 89, the tip of the hook 12 or the cover or main body of the connecting mechanism 82 can be smoothly engaged with the connecting pin 17 without colliding with the top plate 70 and the end surface. In this manner, it is possible to connect the connecting mechanism 82 to the top plate 70 and draw the top plate 70 into the gantry 1 without having an impact on the top plate 70. Therefore, it is possible to ensure the safety of the object 9 on the top plate 70 and to draw the top plate 70 into the gantry 1 without causing a fear of impact.

In addition, since it is sufficient to operate the UP button and the IN button when drawing the top plate 70 into the gantry 1 and it is sufficient to continuously push the OUT button when pulling out the top plate 70 from the gantry 1, it is possible to realize the drawing and pulling out of the top plate 70 by a simple operation.

In addition, although the case where the initial position (home position) of the connecting mechanism 82 is a position other than the origin (for example, near the middle of the gantry 1) has been described as an example in the above embodiment, the origin can also be set as a home position. That is, the connecting mechanism 82 is always located at the origin in a state where the top plate 70 is not connected thereto. In this case, since the operation of steps 204 to 206 in the flowchart of FIG. 9 described above is not necessary, it is possible to simplify the operation of connecting and drawing the top plate as in the flowchart shown in FIG. 12.

In addition, although the timing belt 85 is used in the present embodiment, the present invention is not limited thereto, and any kind of driving mechanism may be used as long as it can move the connecting mechanism 82. For example, the connecting mechanism 82 can also be moved using a ball screw.

<Second Embodiment>

Figure 13:
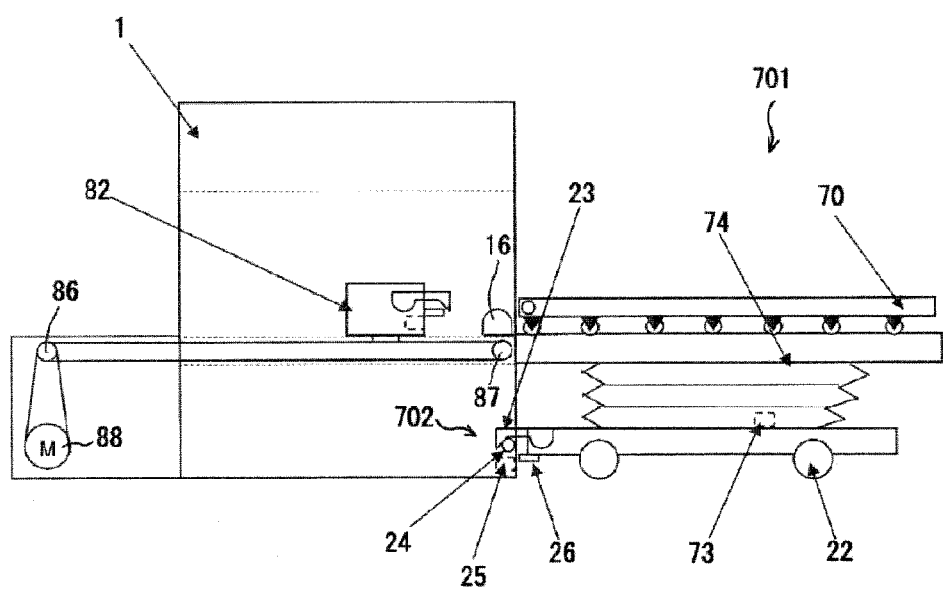
FIG. 13 is a block diagram of a top plate drawing mechanism of a medical image diagnostic apparatus of a second embodiment.

Next, a medical image diagnostic apparatus of a second embodiment will be described. FIG. 13 is a block diagram showing the schematic configuration of the medical image diagnostic apparatus of the present embodiment.

The second embodiment is different from the first embodiment in that a bed device is a movable bed device 701 including a wheel 22. Since each mechanism of the present embodiment is basically the same as in the first embodiment, only the differences from the first embodiment will be described.

A bed connecting mechanism 702 is provided in the movable bed device 701 and the gantry 1. The bed connecting mechanism 702 includes a hook 23 provided in a bed body 74, a connecting rod 24 provided in the gantry 1 so as to be engaged with the hook 23, and a bed connection detection sensor 25 provided in the gantry in order to detect connection with the movable bed device 701. The connection detection sensor 25 detects that a pin 26 provided in the bed body 74 has been pushed into the gantry 1 side by connection with the gantry 1. In addition to these, a connector (not shown) for connecting a signal line, which is for transmitting the output of the vertical position sensor 73 to the control unit 110, or a signal line, which is for receiving the control signal to control the driving mechanism of the movable bed device 701 from the control unit 110, between the gantry 1 and the movable bed device 701 is disposed.

Figure 12:
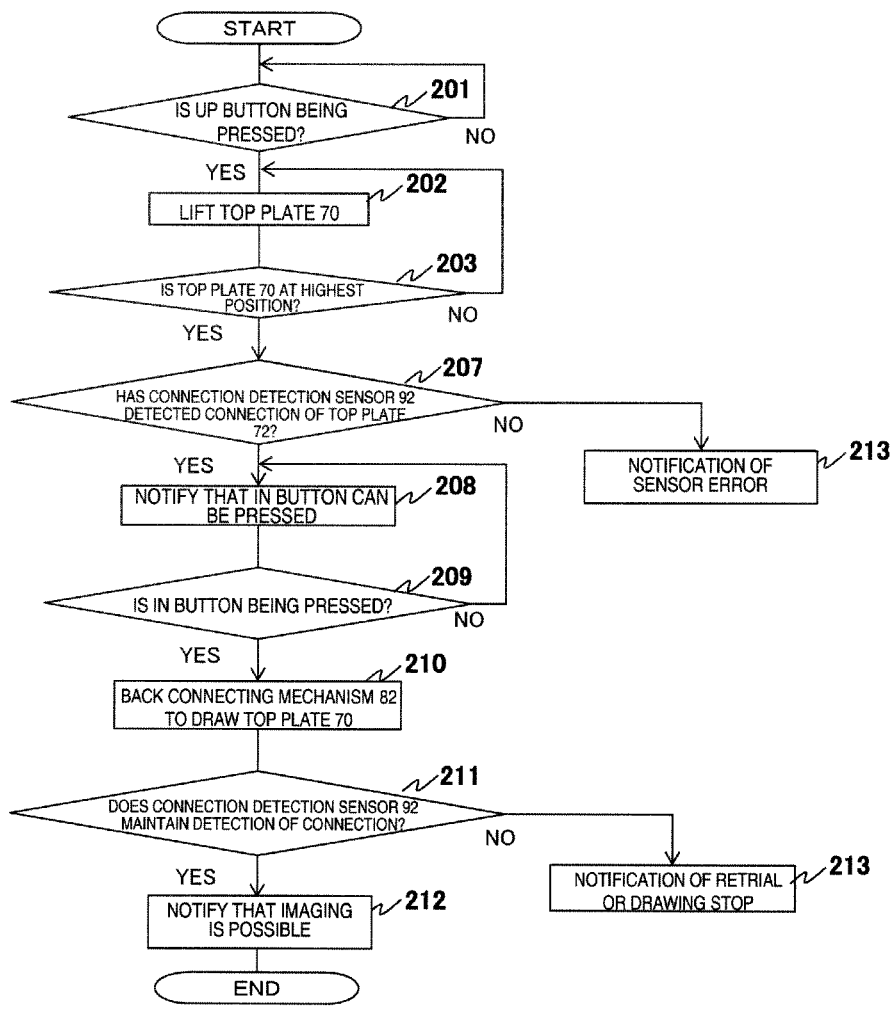
FIG. 12 is a flow chart showing another example of the operation of drawing the top plate 70 into the gantry 1 using the top plate drawing mechanism 8 of the first embodiment.

Only when the bed connection detection sensor 25 detects that the movable bed device 701 has been connected to the gantry 1 through the connecting mechanism 702, step 201 of FIGS. 9 and 12 can be started.

As the bed connection detection sensor 25, it is preferable to use a photosensor (non-contact type) for detecting that the pin 26 has been pushed by the blocking of light. However, it is also possible to use a contact type sensor, such as a microswitch. In addition, instead of the gantry connection detection sensor 25, it is also possible to adopt a configuration to detect the connection electrically by the above-described connector of the signal line.

In addition, it is also possible to attach an electrode pad to each of the hook 23 and the connecting rod 24 of the connecting mechanism 702. In this case, when the hook 23 is engaged with the connecting rod 24, the electrode pads are brought into contact with each other, and accordingly, signal lines of the control signal and the like are electrically connected to each other.

In addition, it is also possible to attach an electrode pad to each of the hook 12 and the connecting pin 17 of the connecting mechanism 82. In this case, when the hook 12 of the connecting mechanism 82 is engaged with the connecting pin 17 of the top plate 70, the electrode pads are brought into contact with each other, and accordingly, signal lines of the control signal and the like are electrically connected to each other.

As described above, according to the medical image diagnostic apparatus of the second embodiment, it is possible to draw the top plate 70 into the gantry even in the case of a movable bed device.

<Third Embodiment>

Figure 14:
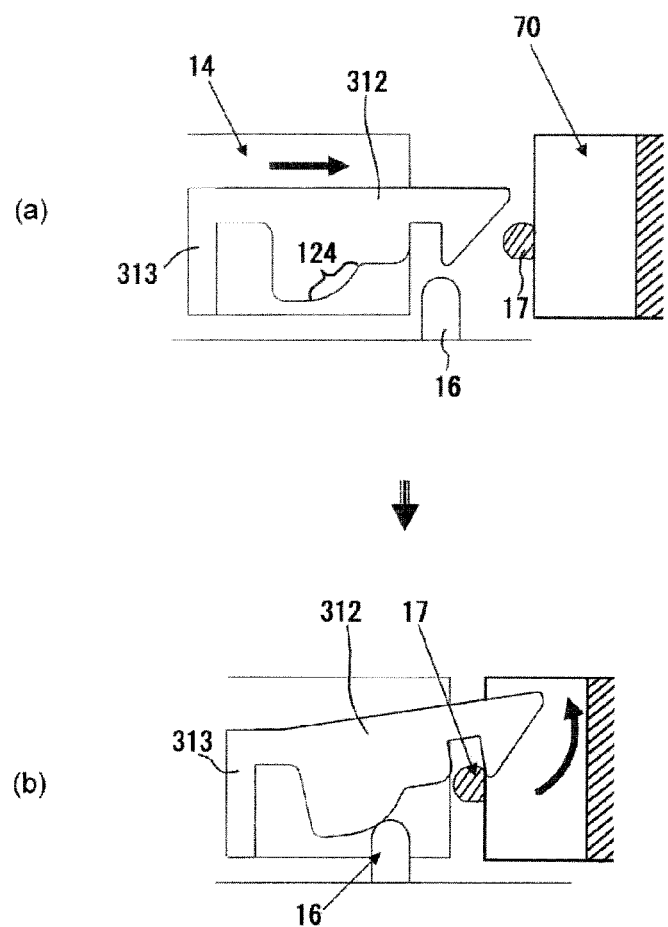
FIGS. 14(a) and 14(b) are explanatory views showing the structure and operation of a hook 12 of a third embodiment.

Next, a medical image diagnostic apparatus of a third embodiment will be described with reference to FIGS. 14(a) and 14(b). FIGS. 14(a) and 14(b) are side views of a hook 312. The difference from the first embodiment is that the elastic member 15 such as a rubber band for biasing the hook 12 downward, the projection 125, and the shaft 13 are not provided, a base portion 313 itself of the hook 312 has a plate spring shape, and an end portion of the plate spring shaped base portion 313 is fixed to the plate portion 14. The hook 312 is biased downward by the elastic force of the plate spring shaped base portion 313. In addition, when the push-up portion 16 rides on the second inclined surface 124, the tip of the hook 312 is lifted above the connecting pin 17 by deformation of the plate spring shaped base portion 313. Since the other configuration is the same as that in the first embodiment, explanation thereof will be omitted.

As described above, according to the third embodiment, the connecting mechanism 82 can be formed using a smaller number of components than in the first embodiment. Therefore, it is possible to reduce the manufacturing cost.

<Fourth Embodiment>

Figure 15:
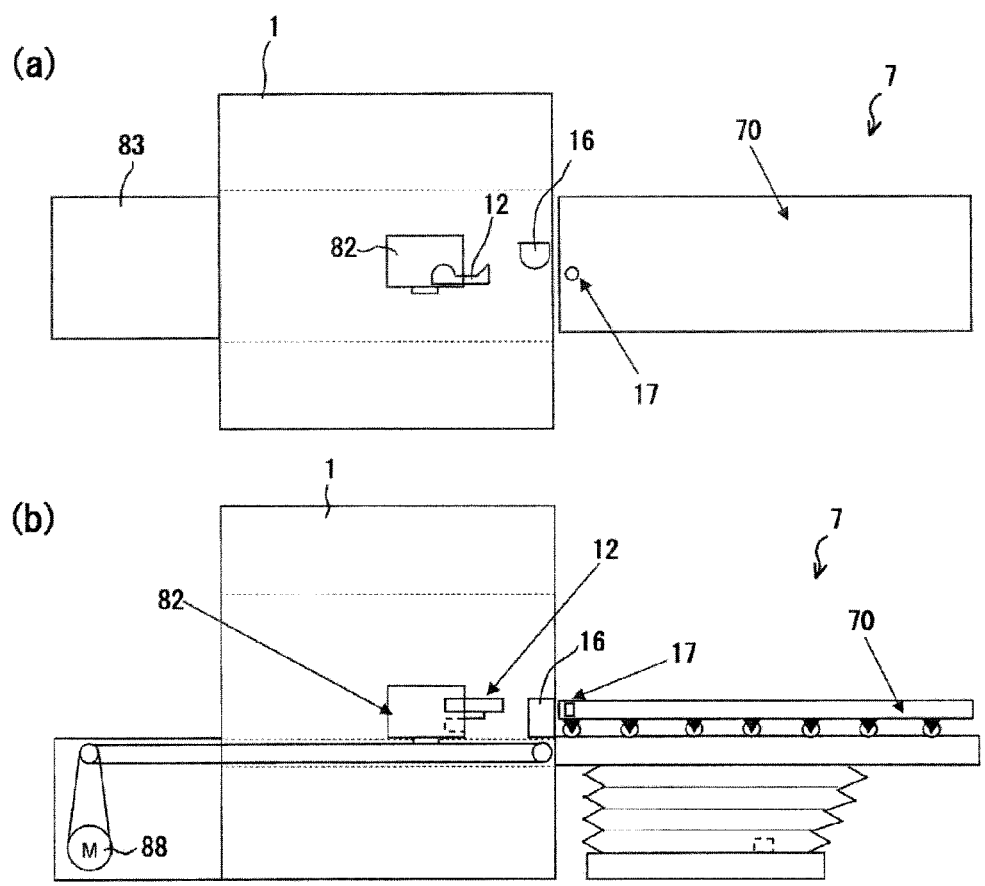
FIG. 15(a) is an explanatory view showing a top plate drawing mechanism of a medical image diagnostic apparatus of a fourth embodiment when viewed from the top surface.
FIG. 15(b) is an explanatory view showing the top plate drawing mechanism of the medical image diagnostic apparatus of the fourth embodiment when viewed from the side surface.

Next, a medical image diagnostic apparatus of a fourth embodiment will be described with reference to FIGS. 15(a) and 15(b). FIG. 15(a) is a block diagram showing the direction of the hook 12 when the connecting mechanism 72 and the bed device 7 are viewed from the top surface, and FIG. 15(b) is a block diagram showing the direction of the hook 12 when viewed from the side surface.

In the fourth embodiment, an opening of the recess 121 of the hook 12 faces horizontally.

Corresponding to this, the connecting pin 17 and the push-up portion 16 are disposed such that the axis direction is parallel to the normal direction of the top plate 70. It is preferable that the connecting pin 17 be disposed within the thickness of the top plate 70. The other configuration is the same as that in the first embodiment.

The connecting mechanism 82 of the present embodiment is connected to the top plate 70 when the hook 12 is caught by the connecting pin 17 disposed within the thickness of the top plate 70. Accordingly, there is an advantage in that the hook 12 does not protrude above the top surface of the top plate 70. For this reason, there is no possibility of contact with the object 9 placed on the top plate 70.

In addition, the recess 121 of the hook 12 may also be made to face upward without being limited to facing downward and horizontally. In this case, the push-up portion 16 is disposed in the top plate receiving portion 81 as a hook push-down portion.

<Fifth Embodiment>

Figure 16:
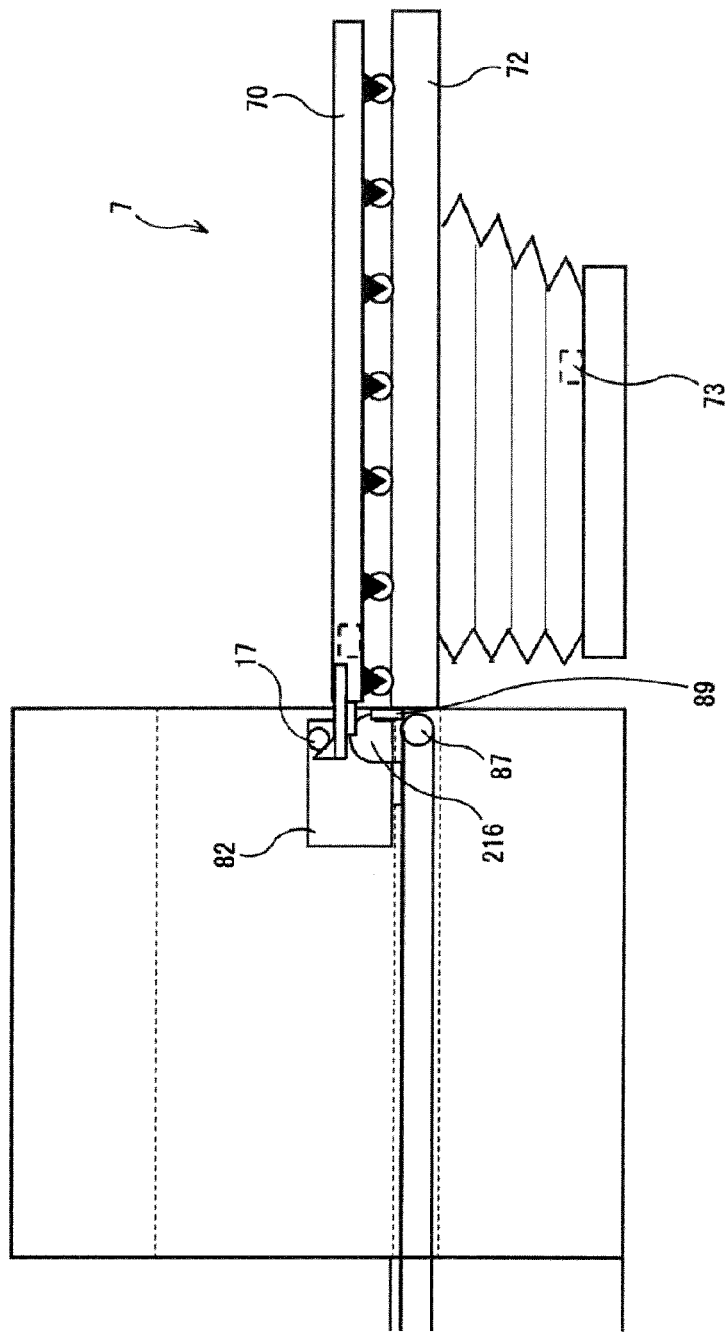
FIG. 16 is a block diagram of a top plate drawing mechanism of a medical image diagnostic apparatus of a fifth embodiment.

Next, a medical image diagnostic apparatus of a fifth embodiment will be described with reference to FIG. 16.

In the fifth embodiment, the hook 12 and the connection detection sensor 92, which are disposed in the connecting mechanism 82 in the first embodiment, are disposed on the end surface of the top plate 70, and the connecting pin 17, which is disposed in the top plate 70 in the first embodiment, is disposed in the connecting mechanism 82. The connecting pin 17 has a movable portion, and is configured to be engaged with the hook 12 when pushed up by a push-up portion 216.

The push-up portion 216 is disposed near the origin of the top plate receiving portion 81 similar to the push-up portion 16 of the first embodiment. The origin sensor 89 is disposed in the top plate receiving portion 81 as in the first embodiment. Since the other configuration is the same as in the first embodiment, explanation thereof will be omitted.

When the top plate 70 rises up to the same height as the top plate receiving portion 81, the connecting mechanism 82 is moved toward the origin. Then, the connecting pin 17 is pushed up in a state of being in contact with the push-up portion 216, and is engaged with the hook 12. When the origin sensor 89 detects the connecting mechanism 82, the connecting mechanism 82 is stopped and moved in a direction away from the bed device 7. As a result, the top plate 70 is connected to the connecting mechanism 82 and is drawn into the gantry 1.

According to the fifth embodiment, the connecting mechanism 82 can always be disposed at the entrance of the gantry 1. Since the hook 12 does not protrude from the gantry 1, the movement of the connecting mechanism 82 toward the origin that is performed in step 204 of FIG. 9 in the first embodiment is not necessary in the fifth embodiment.

In each of the above embodiments, the medical image diagnostic apparatus has been described by way of an example of the MRI apparatus. However, the present invention is not limited to the MRI apparatus, and can be applied to various kinds of apparatuses in which the top plate is moved to a predetermined position. For example, it is possible to apply the top plate drawing mechanism of the present invention to an X-ray imaging apparatus or a CT apparatus.

Reference Signs List

1: gantry
   1a: gantry cover
   7: bed device
   12: hook
   13: shaft
   15: elastic member
   16: push-up portion
   17: connecting pin
   23: hook
   24: connecting rod
   25: bed connection sensor
   26: pin
   70: top plate
   72: top plate support
   73: vertical position sensor
   74: bed device body
   75: wheel
   81: top plate receiving portion
   82: connecting mechanism
   83: top plate receiving portion support
   84: wheel
   85: timing belt
   86, 87: pulley
   88: motor
   89: origin sensor
   90: base
   91: projection
   92: connection detection sensor
   94: traveling surface
   121: recess
   122: first inclined surface
   123: horizontal surface
   124: second inclined surface
   125: projection
   312: hook
   313: base portion of hook 702: bed connecting mechanism
102: magnet
103: gradient magnetic field coil
104: high-frequency magnetic field (RF) coil
105: RF probe
106: gradient magnetic field power supply
107: RF transmission unit
108: signal detection unit
109: signal processing unit
110: control unit
112: operating unit

The invention claimed is:

1. A medical image diagnostic apparatus, comprising:
a gantry having an imaging space;
a bed device including a top plate on which an object is placed; and
a top plate drawing mechanism that draws the top plate into the imaging space of the gantry,
wherein at least a part of the top plate drawing mechanism is disposed in the gantry, and the top plate drawing mechanism includes a top plate receiving portion having an end disposed opposite the bed device, a connecting mechanism that is movable on the top plate receiving portion, and a driving unit that moves the connecting mechanism on the top plate receiving portion,
a first member having a predetermined shape that is engaged with the connecting mechanism is provided in an end portion of the top plate,
a second member having a shape that is engaged with the first member of the top plate and a movable portion that retracts the second member up to a predetermined position are provided in the connecting mechanism, and
the top plate drawing mechanism moves the connecting mechanism toward the bed device on the top plate receiving portion, retracts the second member up to the predetermined position when the connecting mechanism becomes close to a predetermined origin of a top surface on the one end side of the top plate receiving portion, stops the connecting mechanism when the connecting mechanism aches the origin, and releases the retraction of the second member while making the connecting mechanism move away from the bed device, so that the second member is engaged with the first member of the top plate and the top plate is drawn into the gantry.

2. A medical image diagnostic apparatus, comprising:
a gantry having an imaging space;
a bed device including a top plate on which an object is placed; and
a top plate drawing mechanism that draws the top plate into the imaging space of the gantry,
wherein at least a part of the top plate drawing mechanism is disposed in the gantry, and the top plate drawing mechanism includes a top plate receiving portion having an end disposed opposite the bed device, a connecting mechanism that is movable on the top plate receiving portion, and a driving unit that moves the connecting mechanism on the top plate receiving portion,
a first member having a predetermined shape that is engaged with the connecting mechanism is provided in an end portion of the top plate,
a second member having a shape that is engaged with the first member of the top plate and a movable portion that retracts the second member are provided in the connecting mechanism,
in the top plate receiving portion, a projection is provided at a predetermined position near a predetermined origin of a top surface on the one end side, and
the projection is brought into contact with the second member and retracts the second member when the connecting mechanism becomes close to the origin, and is away from the second member to release the retraction when the connecting mechanism moves in a direction away from the origin.

3. The medical image diagnostic apparatus according to claim 2, further comprising:
a control unit that controls the driving unit of the top plate drawing mechanism,
wherein the control unit moves the connecting mechanism toward the bed device on the top plate receiving portion, stops the connecting mechanism when the connecting mechanism reaches the origin, and moves the connecting mechanism in a direction away from the bed device, so that the second member that has been retracted due to the projection is connected to the first member of the top plate and the top plate is drawn into the gantry.

4. The medical image diagnostic apparatus according to claim 3,
wherein the top plate drawing mechanism further includes a connection detection sensor that detects connection between the connecting mechanism and the top plate, and
the control unit moves the connecting mechanism in a direction away from the bed device if the connection detection sensor detects connection when the connecting mechanism has stopped after reaching the origin.

5. The medical image diagnostic apparatus according to claim 3,
wherein the bed device further includes a top plate height sensor that detects a height of the top plate, and
when it is detected from an output of the top plate height sensor that the top plate is located at a same height as the top plate receiving portion, the control unit moves the connecting mechanism toward the bed device on the top plate receiving portion in order to connect the connecting mechanism to the top plate.

6. The medical image diagnostic apparatus according to claim 2,
wherein the top plate drawing mechanism further includes an origin sensor that detects that the connecting mechanism has reached the origin of the top plate receiving portion.

7. The medical image diagnostic apparatus according to claim 2,
wherein the first member is a rod shaped member, and the second member is a hook.

8. The medical image diagnostic apparatus according to claim 2,
wherein the second member is a hook, and
the projection displaces and retracts a tip of the hook with respect to a base portion of the hook by being brought into contact with the hook.

9. The medical image diagnostic apparatus according to claim 8,
wherein the hook has a recess for being engaged with the first member and an inclined surface provided closer to the base portion than the recess is, and
as the connecting mechanism becomes close to the origin, the inclined surface is brought into contact the projection to gradually displace the tip of the hook.

10. A medical image diagnostic apparatus, comprising:
a gantry having an imaging space;
a bed device including a top plate on which an object is placed; and a top plate drawing mechanism that draws the top plate into the imaging space of the gantry, wherein at least a part of the top plate drawing mechanism is disposed in the gantry, and the top plate drawing mechanism includes a top plate receiving portion having an end disposed opposite the bed device, a connecting mechanism that is movable on the top plate receiving portion, and a driving unit that moves the connecting mechanism on the top plate receiving portion, a first member having a predetermined shape that is engaged with the connecting mechanism is provided in an end portion of the top plate, a second member having a shape that is engaged with the first member of the top plate and a movable portion that makes the second member displace are provided in the connecting mechanism, in the top plate receiving portion, a projection is provided at a predetermined position near a predetermined origin of a top surface on the one end side of the top plate receiving portion, and the projection is brought into contact with the second member and displaces the second member when the top plate becomes close to the origin, so that the second member is engaged with the first member and the connecting mechanism and the top plate are connected to each other.

* * * * *